United States Patent [19]

Sze et al.

[11] Patent Number: 4,490,153

[45] Date of Patent: Dec. 25, 1984

[54] PROCESS FOR THE PRODUCTION OF GASOHOL

[75] Inventors: Morgan C. Y. Sze, Portsmouth, N.H.; George D. Suciu, Ridgewood, N.J.

[73] Assignee: Lummus Crest Inc., Bloomfield, N.J.

[21] Appl. No.: 546,871

[22] Filed: Oct. 31, 1983

Related U.S. Application Data

[63] Continuation of Ser. No. 304,476, Sep. 22, 1981, abandoned.

[51] Int. Cl.$^3$ ............................................... C10L 1/02
[52] U.S. Cl. ............................................ 44/56; 44/53; 209/165; 203/52; 203/57; 203/44
[58] Field of Search .................. 44/53, 56; 209/165; 203/52, 57, 44

[56] References Cited

U.S. PATENT DOCUMENTS 2,371,010  3/1945  Wolfner ................................. 44/56
4,251,231  2/1981  Baird ...................................... 44/56

Primary Examiner—Glennon H. Hollrah
Assistant Examiner—Raymond Covington
Attorney, Agent, or Firm—James N. Blauvelt

[57] ABSTRACT

Low energy process for the production of gasoline-ethanol blends, comprising dehydrating the aqueous ethanolic product from a conventional fermentation process, preferably containing about 6 wt. % ethanol, so as to generate an aqueous ethanolic effluent containing about 90 wt. % ethanol; mixing the effluent with gasoline feedstock; chilling the resultant gasoline-aqueous ethanol mixture to a temperature of about −10° F., without forming ice, thereby to form (1) a gasohol blend containing about 10 wt. % ethanol and (2) an aqueous stream comprising some ethanol and traces of gasoline; extracting the gasoline-containing aqueous stream with a minor stream of the fermentation ethanol product in order to recover the gasoline it contains; and recovering said blend to produce a gasohol product under-saturated with water at all operating temperatures above −10° F.

11 Claims, 1 Drawing Figure

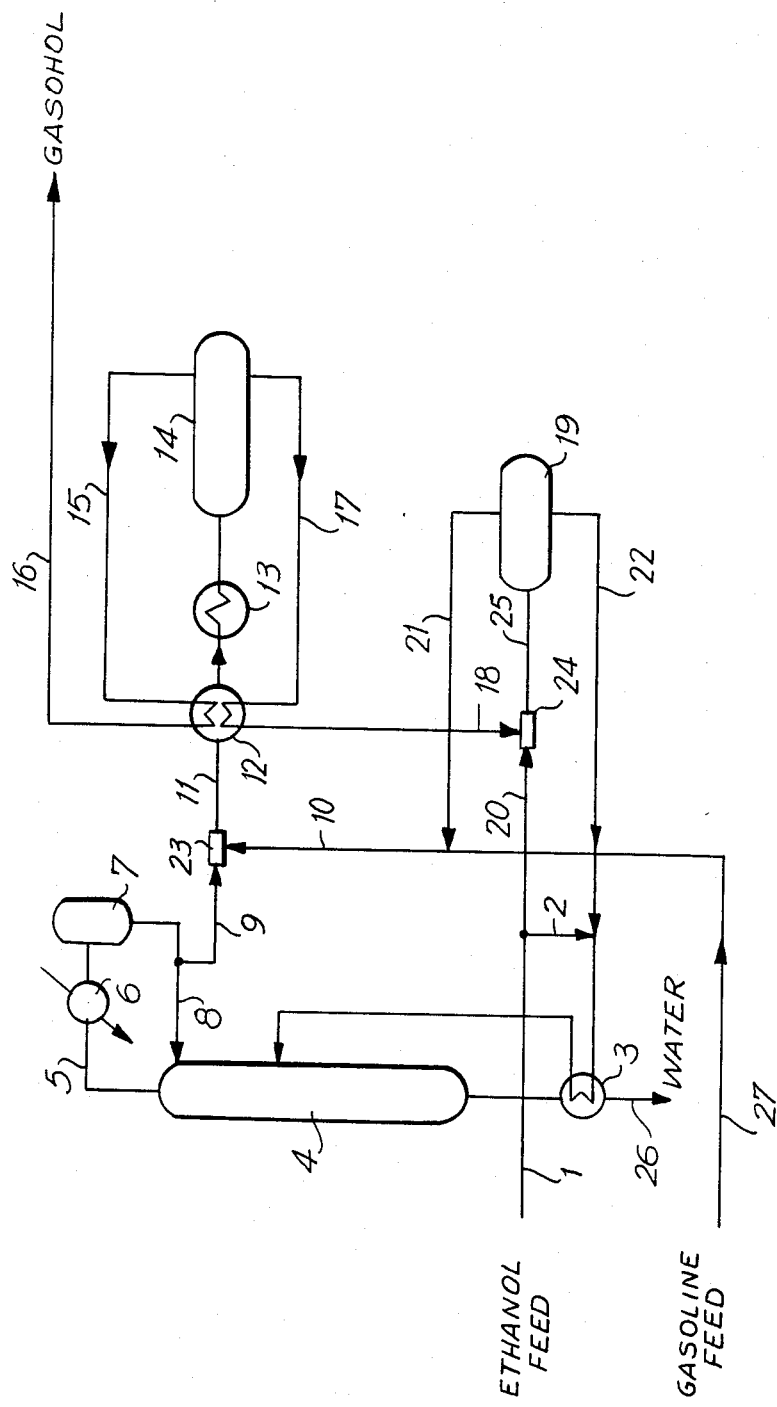

PROCESS FOR THE PRODUCTION OF GASOHOL

This is a continuation of application Ser. No. 304,476, filed Sept. 22, 1981 now abandoned.

BACKGROUND OF THE INVENTION

1. Field of the Invention

The present invention relates generally to the field of automotive fuels, and more particularly to various gasoline-ethanol blends commonly referred to under the broad heading of "gasohol." Gasohol typically comprises blends of up to approximately 10 vol.% ethanol in gasoline, and is considered one of the leading sources for supplementing or replacing petroleum fuels such as gasoline.

More specifically, the present invention relates to a process for the production of such gasoline-ethanol blends by dehydrating an aqueous ethanol, preferably the aqueous ethanolic product from a conventional fermentation process, comprising from about 4 to about 12 wt.% ethanol, preferably about 6 wt.% ethanol, so as to generate an effluent containing about 90 wt.% ethanol; extracting such effluent with a gasoline at a low, sub-ambient temperature, thereby enabling the water concentrations present in the gasohol produced in such process to be carefully controlled and the excess thereof separated from the ultimate gasohol blend and restored to the overall process for purposes of further extraction.

2. Description of the Prior Art

Dehydration of alcohols, particularly of ethanol, is a well-known art, and the methods generally used for such dehydration have either involved use of azeotropic distillation (see, e.g., U.S. Pat. Nos. 2,140,694; 2,173,692; and 2,358,193) or of non-distillation methods exemplified by the use of various adsorbents, such as shown by U.S. Pat. No. 2,137,605. Furthermore, it is also well known in the art that extraction is another method for the dehydration of alcohols or mixtures of alcohols. For example, U.S. Pat. No. 3,052,731 shows the use of hexane to separate, by extraction, water and a mixture of alcohols obtained as a result of partial oxidation. Moreover, in a more specific application of extraction, i.e., with hydrocarbons, U.S. Pat. No. 3,455,664 shows the use of gasoline extraction to achieve dehydration, but such use is essentially shown to be restricted within the context of isopropyl alcohol synthesis, through mixing of the gasoline with the isopropyl alcohol reaction product, and it involves a subsequent separation step conducted under considerable pressure, e.g., a pressure greater than 2,000 p.s.i.

It is also known to make gasoline and alcohol blends and utilize such blends in internal combustion engines of the Otto type, i.e., those which use spark plugs. For example, U.S. Pat. No. 1,699,355 discloses treating gasoline with alcohols to prevent "knocking" in internal combustion engines. However, the resultant gasohol product contains too much water for today's motor fuel standards since it has been saturated with water at temperatures in excess of those which might be encountered during the operation of the engine and thus might generate an undesired water phase upon occasional cooling. On the other hand, the prior art, including that which has been discussed above, has been generally of the opinion that the costs of energy consumption needed to produce gasohol by heretofore conventional means are too high, thereby making gasohol too costly an alternative to gasoline for use as fuel. In addition, control of the water content in gasohol blends, an element vital to the successful use of such blends as fuels for internal combustion engines, and removal of excess water from conventionally produced gasohol blends by known means, involve additional cost and separation problems, associated with increased capital investments and energy consumption.

The present invention, however, is quite adept at filling all these prior art voids in that it greatly reduces the amount of energy necessary to produce gasohol while concurrently providing means for achieving acceptable water levels in the gasohol produced. Because the distillation of ethanol from a 6 weight % fermentation feed to a 90 weight % effluent product ethanol requires relatively low energy consumption, much lower, for example, than the energy required for producing 95 weight % ethanol or anhydrous ethanol, this factor can be exploited to great advantage by producing gasohol directly from blending such 90 weight % effluent ethanol with a conventional gasoline or gasoline source. In this manner, the overall energy consumption involved in the production of gasohol is significantly reduced when compared to the energy consumed by known and/or previously used methods for producing gasohol.

Moreover, since it is also well known that gasohol blends must not have a water content so high as to cause the separation of an aqueous phase during storage, transportation, distribution, and use, the fact that the present invention solves this problem concurrently while providing means for greatly reducing the energy consumption required to produce gasohol makes the present process for producing gasohol quite attractive commercially.

Through deployment of appropriately situated heat exchangers in the overall process, moreover, energy consumption and costs related to the cooling process can also be sharply reduced.

SUMMARY OF THE INVENTION

The present invention accordingly provides a more efficient (particularly energy efficient) and a less costly process for the production of gasohol than has been known heretofore. It utilizes a source of dilute aqueous ethanol (e.g., fermentation ethanol) for the purposes of gasohol production, and also employs a commercially feasible means of converting (e.g., rectification) such ethanol to 90 weight % ethanol. The resultant 90 weight % ethanol can then be used to produce gasohol directly via low temperature extraction of such aqueous ethanol with a gasoline. Thereafter, means are provided, including specific cooling means, for separating and removing the water in excess of that soluble at the temperature at which the gasohol product separates into phases. The excess water removed can be used elsewhere, thereby enhancing the economics of the overall process. Such specific cooling means comprises a two-stage cooling scheme which makes possible the operation at the low temperatures required in order that the gasohol product have a water content which is compatible with its use as a motor fuel.

BRIEF DESCRIPTION OF THE DRAWING

The above and other features and advantages of the present invention will become more readily apparent from the following description of the invention, when viewed in light of the FIGURE of the present drawing. This FIGURE depicts broadly the preferred process of the present invention for producing gasohol, and illustrates it in the form of a schematic flow diagram.

DESCRIPTION OF THE PREFERRED EMBODIMENTS

It is to be understood that certain equipment such as pumps, valves, indicators, and the like have been omitted from the drawing so as to facilitate the description thereof and that the placement of such equipment at appropriate places in the process is deemed to be within the scope of those skilled in the art.

With reference to the FIGURE, a crude aqueous ethanol feed such as one derived from a conventional ethanol fermentation process and containing about 4%–12% by volume ethanol, preferably filtered, is introduced into the present process and pumped (by a means not shown) through line 1. The major stream 2 of this feed is then passed through heat exchanger 3 and fed to a distillation column or tower 4 wherein it is rectified to a point such that an overhead stream containing at least about 75 mole %, and preferably about 78 mole % (i.e., 90 weight %), ethanol is generated. This overhead stream is passed, via line 5, through heat exchanger 6—which functions as a condenser, condensing sufficient liquid to satisfy reflux requirements of the distillation column 4—into reflux vessel 7, from which a portion returns, via line 8, to the distillation tower 4.

Most of the condensate stream, however, is brought, through line 9, into contact with a stream 10 of a gasoline feedstock in the mixer 23 and passed, via line 11, into a heat exchanger 12 where the resultant mixture is chilled to a temperature of preferably approximately +5° F. by exchange with the streams of cold gasohol 15 and of cold aqueous phase 17 coming from a decanter vessel, first settler 14. The purpose of this chilling step is to recover a significant portion of the energy which is spent for bringing the process streams to the temperature required by the present invention, and to reheat the finite gasohol stream and the spent aqueous stream back to temperatures close to the ambient.

The chilled bisphasic mixture is then passed into heat exchanger 13 (which can be refrigerated with a suitable refrigerant such as propane) where it is further cooled to a temperature of about −10° F. The effect of such additional cooling is to expel from the organic phase most of the water it contains.

The cooled mixture is then passed into first settler 14 wherein it becomes separated into two discrete phases: one phase comprises a gasohol blend, comprising gasoline, about 10 weight % ethanol, and traces of water; the other phase comprises ethanol and significant amounts of water and gasoline.

From this first settler, gasohol, at a temperature of −10° F., containing approximately 10 weight % alcohol and saturated with water, is removed, via line 15, and passed through heat exchanger 12, where it is warmed to ambient temperature. The resultant gasohol product is then passed, via line 16, into a storage and distribution system for commercial gasohol.

The cold aqueous phase from the first settler 14, and which, as noted, contains significant amounts of gasoline, is passed, via line 17, through heat exchanger 12, where it precools stream 11, and is mixed in mixer 24 with a fraction of the aqueous ethanol feed which arrives through line 20. The mixed streams enter another decanter vessel, second settler 19, via line 25. The organic phase which is separated leaves the second settler 19 through line 21 and is mixed in line 10 with the gasoline feed.

The aqueous phase separated in decanter 19 contains a small amount of ethanol and only traces of gasoline. It leaves decanter 19 through line 22 and, after mixing with a portion of the fresh aqueous ethanol arriving through line 2 and being preheated in the bottoms cooler 3 by the hot column bottom product 26, is fed to column 4.

The column bottom product 26 consists of essentially pure water which can be used as feed to the fermentation unit, or as may be desired.

One of the most attractive features of the present invention is that it combines, into one overall low energy process, several independent and distinct features never before combined. This fortuitous combination of features now satisfies a long-felt, hitherto unsatisfied need in the art. The present invention now makes available a commercially attractive means for economically producing gasohol, comprising: (a) generating a low energy consumption form of an aqueous ethanol (i.e., 90 wt.% ethanol) that is not suitable per se for a number of commercial applications and processes in which ethanol is employed, owing to its high water content; and (b) exploiting the cost advantages associated with this form of ethanol or its method of manufacture by making gasohol therefrom through extraction with gasoline and removal of excess water through selective cooling techniques so as to prevent the formation of an aqueous phase in the ultimate gasohol product.

By the term "gasoline," wherever and whenever used herein, is meant a variety of hydrocarbon mixtures all of which have in common the capability of being suitable for use in internal combustion engines, preferably those having a high compression ratio, and most preferably those of the Otto type.

As previously noted, the "front end" of the present process is concerned with the obtainment of a 90 wt.% aqueous ethanol, preferably derived from a conventional fermentation process (wherein almost any agricultural raw material with a carbohydrate content in the form of sugars, or starches easily converted to sugars, can be used). The obtainment of this level of aqueous ethanol concentration is usually achieved by dehydration of a much more dilute precursor form such as 4–12 wt.% aqueous ethanol. As is known in the art, dehydration of aqueous alcohols is usually achieved in one of two ways: distillation methods or non-distillation methods. Distillation of aqueous ethanols has usually proceeded via rectification of the binary water-ethanol azeotrope or of a corresponding ternary azeotrope (when a third component, soluble in ethanol but not in water, has been added to the binary water-ethanol azeotrope.) Suitable representative examples of the third component include ethyl ether, diisopropyl ether, pentane, cyclohexane, etc.

Customarily, conventional (e.g. "thermal") distillation is used to dehydrate the aqueous ethanol to a concentration of 95 wt.% ethanol. Then, this is ordinarily followed by azeotropic distillation, in which the third component is added to permit complete separation of the ethanol and water. By means of the present invention, the second distillation step is eliminated and the first is restricted to the production of 90 wt.% (rather than 95 wt.%) aqueous ethanol. The distillation of aqueous ethanol to 90 wt.% ethanol requires much less energy consumption than is required for producing 95 wt.% ethanol.

Non-distillation methods of dehydrating aqueous alcohols have centered upon the use of adsorbents to dry ethanol, or upon the use of extraction, with either conventional solvents or supercritical ones. Suitable representative examples of such adsorbents include alumina, clinoptilolite, zeolite sodium-A, bauxite, fuller's earth, and acid-activated bentonite. For purposes of this invention, however, the best mode of operation of the present process resides in dehydration of aqueous alcohols, through distillation, to 90 wt.% ethanol. Nevertheless, the extraction aspects of this invention, at sub-ambient temperatures, with a gasoline solvent, can be applied to any 90 wt.% aqueous ethanol, regardless of its method of manufacture.

Accordingly, in a preferred embodiment of this invention there is provided a process for the production of gasoline-ethanol blends by dehydrating, preferably by rectifying, the aqueous ethanolic product from a conventional fermentation process containing about 4–12 wt.% ethanol, preferably about 6 wt.% ethanol, so as to generate an aqueous effluent containing about 90 wt.% ethanol; mixing such effluent with a gasoline solvent; chilling the resulting gasoline-aqueous ethanol mixture to a sub-ambient temperature, preferably to a temperature ranging from +5° F. to −10° F. so as to obtain an organic phase consisting of the gasohol blend, which contains approximately 10% wt. ethanol, and an aqueous phase containing some ethanol and traces of gasoline; mixing the aqueous phase with a stream of fresh aqueous ethanolic product; decanting the resulting mixture to form an organic phase and an aqueous phase; mixing the organic phase with the feed to the first extraction stage; mixing the aqueous phase with the main stream of the aqueous ethanolic product; and feeding the resulting mixture to the initial distillation stage for the production of 90% aqueous ethanol.

In the best mode of the present invention, there is provided a low energy process for the production of gasohol, in various gasoline-ethanol blends, which comprises rectifying a dilute aqueous ethanolic solution containing about 6 wt.% ethanol to an extent sufficient to generate an aqueous effluent containing about 90 wt.% ethanol; extracting, in a first stage, the resultant ethanol with a gasoline; cooling the resultant gasoline-ethanol admixture to a temperature of about −10° F.; passing the cooled admixture to a first settler; recovering from said settler a gasohol phase saturated with water and containing 10 wt.% ethanol and heat exchanging the recovered gasohol; recovering the aqueous phase from said first settler containing a minor amount of gasoline; heat exchanging said recovered aqueous phase; extracting said heat exchanged aqueous phase with fresh dilute aqueous ethanol in a second settler; mixing the organic phase from said second settler with a fresh gasoline solvent; feeding the organic phase-gasoline mixture to the first extraction stage; and adding the aqueous phase from said second settler to the aqueous ethanol feedstock introduced into the rectification stage.

EXAMPLES OF THE INVENTION

The following two examples are illustrative of the process of the present invention. They refer to the FIGURE which represents a process flow diagram according to the present invention.

EXAMPLE 1

In this example, for comparison purposes, the process is performed without cooling.

The compositions corresponding to stream 11 were simulated by mixing appropriate amounts of ethanol, water, and gasoline. After decanting, the phases were separated, weighted, and analyzed. The concentration of ethanol and gasoline in both phases was determined by gas chromatography. The concentration of the water in the organic phase (stream 16) was determined by the Karl Fischer method.

The same procedure was followed in order to simulate the stream 25 and its phase separation.

On the basis of the above measurements, performed at approximately room temperature, the flows and composition presented in the accompanying Table 1 were calculated. The concentration of the water measured in the gasohol stream was 0.39 wt.%.

TABLE I

| STREAM NO. | FEED (1) | | | WATER LAYER FROM FIRST SETTLER (18) | | | FEED TO SECOND SETTLER (25) | | |
|---|---|---|---|---|---|---|---|---|---|
| | M/H | #/H | WT. % | M/H | #/H | WT. % | M/H | #/H | WT. % |
| H$_2$O | 4260.0 | 76680 | 93.86 | 20.0 | 360.2 | 25.3 | 472.7 | 8508.9 | 84.2 |
| ETOH | 109.0 | 5014 | 6.14 | 20.5 | 941.2 | 66.1 | 32.1 | 1475.1 | 14.6 |
| GASOLINE (25% Aromatics) | — | — | — | 1.1* | 122.5 | 8.6 | 1.1 | 122.5 | 1.2 |
| TOTAL | 4369.0 | 81694 | 100.0 | 41.6 | 1423.9 | 100.0 | 505.9 | 10106.5 | 100.0 |
| P - PSIG | | 50 | | | 50 | | | 45 | |
| T - °F. | | 115° | | | 85° | | | 110° | |

| STREAM NO. | OIL LAYER FROM SECOND SETTLER (21) | | | WATER LAYER FROM SECOND SETTLER (22) | | | OVERHEAD FROM COLUMN (5) | | | GASOLINE TO PLANT (27) | | |
|---|---|---|---|---|---|---|---|---|---|---|---|---|
| | M/H | #/H | WT. % | M/H | #/H | WT. % | M/H | #/H | WT. % | M/H | #/H | WT. % |
| H$_2$O | — | 1.0 | 1.0 | 472.7 | 8507.9 | 85.1 | 28.0 | 503.2 | 10.0 | — | — | — |
| ETOH | — | 1.1 | 1.0 | 32.1 | 1474.0 | 14.7 | 98.5 | 4529.2 | 90.0 | — | — | — |
| GASOLINE (25% Aromatics) | 0.9 | 102.5 | 98.0 | 0.2 | 20.0 | 0.2 | .2 | 20.0 | — | 297.6 | 32739 | 100.0 |
| TOTAL | 0.9 | 104.6 | 100.0 | 505.0 | 10001.9 | 100.0 | 126.7 | 5052.4 | 100.0 | 297.6 | 32739 | 100.0 |
| P - PSIG | | 75 | | | 75 | | | 75 | | | 75 | |
| T - °F. | | 110° | | | 110° | | | 100° | | | 100° | |

| STREAM NO. | GASOLINE TO FIRST SETTLER (10) | | | GASOHOL (16) | | | WATER LAYER FROM 1st SETTLER (17) | | | WASTE WATER TO FERMENTATION (26) | | |
|---|---|---|---|---|---|---|---|---|---|---|---|---|
| | M/H | #/H | WT. % | M/H | #/H | WT. % | M/H | #/H | WT. % | M/H | #/H | WT. % |

TABLE I-continued

| | | | | | | | | | | | | |
|---|---|---|---|---|---|---|---|---|---|---|---|---|
| H₂O | — | 1.0 | — | 7.9 | 143 | 0.4 | 20.0 | 360.2 | 25.3 | 4252.1 | 76537 | 98.2 |
| ETOH | — | 1.1 | — | 78.0 | 3588 | 9.8 | 20.5 | 941.2 | 66.1 | 31.0 | 1426 | 1.8 |
| GASOLINE | 298.5 | 32841.5 | 100.0 | 297.6 | 32739 | 89.8 | 1.1 | 122.5 | 8.6 | — | — | — |
| (25% Aromatics) TOTAL | 298.5 | 32843.6 | 100.0 | 383.5 | 36470 | 100.0 | 41.6 | 1423.9 | 100.0 | 4283.1 | 77963 | 100.0 |
| P - PSIG | | 75 | | | 75 | | | 50 | | | | |
| T - °F. | | 100° | | | −10° | | | 75° | | | | |

*Av. M. Wt. 110

EXAMPLE 2

The procedure described above for the simulation of the composition and phase separation of stream 11 was repeated at the temperature of −9.4° F. (−23° C.) The measured and calculated compositions of the various streams are given in Table 2. The most significant difference from the results of Table 1 is that the water content of the gasohol (stream 16) is now 0.15 wt.% (by the Karl Fischer method).

Thus, by performing the extraction at −9.4° F. the concentration of water in the gasohol was reduced by most of the water it contains. At this temperature, such expulsion can be effected without forming ice. If one proceeds to a temperature lower than −10° F., however, the possibility or likelihood of ice formation increases. Although the ice that may form at temperatures lower than −10° F. would constitute no problems for those skilled in the art to remove, it nevertheless does entail additional work and perhaps additional equipment as well to accommodate its removal. Thus, cooling to a temperature of lower than −10° F., say, e.g., −11° F. to −20° F., is not as preferred as cooling to the limit of −10° F., for the above reasons.

| | FEED (1) | | | WATER LAYER FROM FIRST SETTLER (18) | | | FEED TO SECOND SETTLER (25) | | |
|---|---|---|---|---|---|---|---|---|---|
| STREAM NO. | M/H | #/H | WT. % | M/H | #/H | WT. % | M/H | #/H | WT. % |
| H₂O | 4260.0 | 76680 | 93.86 | 24.4 | 440.2 | 29.3 | 472.7 | 8508.9 | 84.2 |
| ETOH | 109.0 | 5014 | 6.14 | 20.5 | 941.2 | 62.6 | 32.1 | 1475.1 | 14.6 |
| GASOLINE | — | — | — | 1.1* | 122.5 | 8.1 | 1.1 | 122.5 | 1.2 |
| (25% Aromatics) TOTAL | 4369.0 | 81694 | 100.0 | 46.0 | 1503.9 | 100.0 | 505.9 | 10106.5 | 100.0 |
| P - PSIG | | 50 | | | 50 | | | 45 | |
| T - °F. | | 115° | | | 85° | | | 110° | |

| | OIL LAYER FROM SECOND SETTLER (21) | | | WATER LAYER FROM SECOND SETTLER (22) | | | OVERHEAD FROM COLUMN (5) | | | GASOLINE TO PLANT (27) | | |
|---|---|---|---|---|---|---|---|---|---|---|---|---|
| STREAM NO. | M/H | #/H | WT. % | M/H | #/H | WT. % | M/H | #/H | WT. % | M/H | #/H | WT. % |
| H₂O | — | 1.0 | 1.0 | 477.1 | 8587.9 | 85.2 | 28.0 | 503.2 | 10.0 | — | — | — |
| ETOH | — | 1.1 | 1.0 | 32.1 | 1474.0 | 14.6 | 98.5 | 4529.2 | 90.0 | — | — | — |
| GASOLINE | 0.9 | 102.5 | 98.0 | 0.2 | 20.0 | 0.2 | .2 | 20.0 | — | 297.6 | 32739 | 100.0 |
| (25% Aromatics) TOTAL | 0.9 | 104.6 | 100.0 | 509.4 | 10081.9 | 100.0 | 126.7 | 5052.4 | 100.0 | 297.6 | 32739 | 100.0 |
| P - PSIG | | 75 | | | 75 | | | 75 | | | 75 | |
| T - °F. | | 110° | | | 110° | | | 100° | | | 100° | |

| | GASOLINE TO FIRST SETTLER (10) | | | GASOHOL (16) | | | WATER LAYER FROM 1st SETTLER (17) | | | WASTE WATER TO FERMENTATION (26) | | |
|---|---|---|---|---|---|---|---|---|---|---|---|---|
| STREAM NO. | M/H | #/H | WT. % | M/H | #/H | WT. % | M/H | #/H | WT. % | M/H | #/H | WT. % |
| H₂O | — | 1.0 | — | 3.5 | 63 | 0.2 | 24.4 | 440.2 | 29.3 | 4256.5 | 76617 | 98.2 |
| ETOH | — | 1.1 | — | 78.0 | 3588 | 9.9 | 20.5 | 941.2 | 62.6 | 31.0 | 1426 | 1.8 |
| GASOLINE | 298.5 | 32841.5 | 100.0 | 297.6 | 32739 | 89.9 | 1.1 | 122.5 | 8.1 | — | — | — |
| (25% Aromatics) TOTAL | 298.5 | 32843.6 | 100.0 | 379.1 | 36390 | 100.0 | 46.0 | 1503.9 | 100.0 | 4287.5 | 78043 | 100.0 |
| P - PSIG | | 75 | | | 75 | | | 50 | | | | |
| T - °F. | | 100° | | | −10° | | | −10° | | | | |

*Av. M. Wt. 110 more than 60% compared to that which was obtained at room temperature.

While the present invention has been described and illustrated with exemplary embodiments, it will be understood that many modifications will be apparent to those of ordinary skill in the art and that this invention is intended to cover such modifications or any adaptations or variations thereof, especially as defined by the following claims. For example, one such modification would be to cool to a sub-ambient temperature lower than −10° F., e.g. to −20° F. As will be recalled, however, the essential purpose of cooling to a temperature of about −10° F. is to expel from the organic phase

What is claimed is:

1. A process for the production of a gasoline-ethanol fuel for internal combustion engines, comprising the steps of:
   (a) dehydrating a dilute aqueous ethanol solution to an extent sufficient to produce an aqueous ethanolic product containing about 90 weight percent ethanol;
   (b) contacting said ethanolic product with a gasoline;
   (c) cooling the resulting gasoline-ethanolic product admixture comprising an organic phase and an aqueous phase to a subambient temperature sufficient to expel from said organic phase most of the water it contains without forming ice;

(d) separating the resultant organic phase comprising a major amount of gasoline and ethanol from the resultant aqueous phase comprising a minor amount of gasoline; and (e) recovering the resultant gasoline-ethanol product suitable for use as said fuel.

2. A process according to claim 1, wherein the aqueous phase of step (d) is contacted with said dilute aqueous ethanol solution and the gasoline contained in said aqueous phase is recovered.

3. A process according to claim 1, wherein the cooling step (c) is effected in two separate stages, first by chilling the gasoline-ethanolic product admixture to a sub-ambient temperature of about $+5°$ F. andd then by further cooling the chilled admixture to a temperature of about $-10°$ F.

4. A process according to claim 2, wherein the resultant aqueous phase is recycled to step (a).

5. A process for the production of a gasoline-ethanol fuel for internal combustion engines, comprising the steps of:

(a) rectifying a dilute aqueous ethanol solution to an extent sufficient to produce an aqueous ethanolic product containing about 90 weight percent ethanol;

(b) contacting said ethanolic product with a gasoline;

(c) cooling the resulting gasoline-ethanolic product admixture to a sub-ambient temperature of between about $+5°$ F. and about $-10°$ F. without forming ice;

(d) separating the resultant organic phase comprising a major amount of gasoline and ethanol from the resultant aqueous phase comprising a minor amount of gasoline; and (e) recovering the resultant gasoline-ethanol product suitable for use as said fuel.

6. A process according to claim 5, wherein the aqueous phase of step (d) is contacted with said dilute aqueous ethanol solution and the gasoline contained in said aqueous phase is recovered.

7. A process according to claim 6, wherein the recovered gasoline is recycled to step (b).

8. A process according to claim 5, wherein the cooling step (c) is effected in two separate stages, first by chilling the gasoline-ethanolic product admixture to a sub-ambient temperature of about $+5°$ F. and then by further cooling the chilled admixture to a temperature of about $-10°$ F.

9. A process according to claim 5, wherein the organic phase of step (d) is heat exchanged with the admixture of step (c).

10. A process according to claim 5, wherein the aqueous phase of step (d) is heat exchanged with the admixture of step (c) before being contacted with said dilute aqueous ethanol solution.

11. A process according to claim 5, wherein said dilute aqueous ethanol solution is a fermentation ethanolic product.

* * * * *